United States Patent [19]

McFarland et al.

[11] Patent Number: 5,962,252

[45] Date of Patent: Oct. 5, 1999

[54] ASSAY USING MARKED MICROBIAL HOST CELL STRAINS

[75] Inventors: Nancy C. McFarland, Hillsborough; James R. Swartz, Menlo Park, both of Calif.

[73] Assignee: Genentech, Inc., South San Francisco, Calif.

[21] Appl. No.: 08/926,527

[22] Filed: Sep. 10, 1997

Related U.S. Application Data

[62] Division of application No. 08/741,726, Oct. 31, 1996, abandoned.

[51] Int. Cl.$^6$ .............................. C12Q 1/04; C12Q 1/02
[52] U.S. Cl. ................................................ 435/34; 435/29
[58] Field of Search ........................................ 435/29, 34

[56] References Cited

U.S. PATENT DOCUMENTS

| | | | |
|---|---|---|---|
| 2,820,742 | 1/1958 | Pelligrino | 435/454 |
| 3,171,793 | 3/1965 | Searcy et al. | 435/34 |
| 4,729,954 | 3/1988 | Lacks et al. | 435/6 |
| 5,134,063 | 7/1992 | Bochner | 435/29 |
| 5,288,931 | 2/1994 | Chang et al. | 530/399 |
| 5,342,763 | 8/1994 | Swartz | 435/69.1 |

FOREIGN PATENT DOCUMENTS 704538  4/1996  European Pat. Off. .

OTHER PUBLICATIONS

Bader et al., "Multiuse Manufacturing Facilities for Biologicals" *BioPharm* 5:32–40 (Sep. 1992).
Carlson, "Regulation of Sugar Utilization in Saccharomyces Species" *J. Bacteriology* 169(11):4873–4877 (Nov. 1987).
Carlson et al., "Mutants of Yeast Defective in Sucrose Utilization" *Genetics* 98:25–40 (May 1981).
Carlson et al., "Organization of the SUC Gene Family in Saccharomyces" *Molecular & Cellular Biology* 3(3):351–359 (Mar. 1983).
Davidson et al., "Overproduction, Solubilization, and Reconstitution of the Maltose Transport System from *Escherichia coli*" *Journal of Biological Chemistry* 265(8):4254–4260 (1990).
Davis et al. *Microbiology*, Philadelphia:Harper & Row vol. 3rd edition:646–650 (1980).
Gancedo et al., "Energy–Yielding Metabolism" *The Yeasts*, 2nd edition, Academic Press vol. 3, Chapter 6:205–212 (1989).
Goldenthal et al., "Isolation and Characterization of a Maltose Transport Mutant in the Yeast *Saccharomyces cerevisiae*" *Current Genetics* 7:195–199 (1983).
Hopwood et al., "The Streptomyces Genome" *The Bacterial Chromosome*, Drlica and Riley, eds., Washington, DC:American Society for Microbiology,Chapter 10:147–162 (1990).

Kieser et al., "Genetic Manipulation of Streptomyces: Integrating Vectors and Gene Replacement" *Meth. Enzymol.* 204:430–458 (1991).
Liu et al., "An Efficient Screen for Peroxisome–Deficient Mutants of *Pichia pastoris*" *J. Bacteriology* 174(15):4943–4951 (Aug. 1992).
Lopilato et al., "D–ribose metabolism in *Escherichia coli* K–12: genetics, regulation, and transport" *J. Bacteriology* 158(2):665–673 (1984).
Michels et al., "The Dispersed, Repeated Family of MAL Loci in Saccharomyces spp." *J. Bacteriology* 157(3):949–952 (Mar. 1984).
Moralejo et al., "Sequencing and Characterization of a Gene Cluster Encoding the Enzymes for L–Rhamnose Metabolism in *Escherichia coli* " *J. Bacteriology* 175(17):5585–5594 (Sep. 1993).
Needleman et al., "Repeated Family of Genes Controlling Maltose Fermentation in *Saccharomyces carlsbergensis*" *Molecular & Cellular Biology* 3:796–802 (May 1983).
Petering et al., "The *Escherichia coli* β–Glucuronidase Gene as a Marker for Saccharomyces Yeast Strain Identification" *Am. J. Enol. Vitic.* 42(1):6–12 (1991).
Prosser et al., "Luminescence–Based Systems for Detection of Bacteria in the Environment" *Critical Reviews in Biotechnology* 16(2):157–183 (1996).
Redenbach et al., "A set of ordered cosmids and a detailed genetic and physical map for the 8 Mb Streptomyces coelicolor A3(2) chromosome" *Molecular Microbiology* 21(1):77–96 (1996).
Ugarova et al., "Bioluminescence and Bioluminescent Analyses: Recent Developments in the Field" *Biokhimiya* 58(9):1351–1372 (1993).
Vezinhet et al., "Yeast Genetic Labeling: Checking Tool for Pure Strain Fermentations" *Bull. O.I.V.* 643–644:759–773 (1984).

*Primary Examiner*—Ponnathapura Achutamurthy
*Assistant Examiner*—Elizabeth Slobodyansky
*Attorney, Agent, or Firm*—Janet E. Hasak

[57] ABSTRACT

An assay is provided for determining the presence of contaminating microbial host cells in a culturing vessel containing a microbial host cell strain that utilizes more than one carbohydrate source as a substrate comprising:

(a) culturing the microbial host cell strain in the vessel, wherein the strain comprises nucleic acid encoding a polypeptide of interest and is genetically marked so as not to utilize a carbohydrate source as a substrate;

(b) plating an isolated sample of culture from step (a) onto culture media supplemented with a carbohydrate source not utilized by the host cell strain as a substrate;

(c) incubating the plated cells at a temperature and for a time sufficient for any positive colony to grow to a detectable level; and (d) detecting whether any colonies are growing on the supplemented culture media.

2 Claims, No Drawings

ASSAY USING MARKED MICROBIAL HOST CELL STRAINS

This is a divisional of application Ser. No. 08/741,726 filed on Oct. 31, 1996, abandoned, which application is incorporated herein by reference and to which application priority is claimed under 35 USC §120.

BACKGROUND OF THE INVENTION

1. Field of the Invention

This invention relates to an assay involving genetically marked production host cell strains that are routinely the source of the manufacture of recombinantly produced proteins in a multiple-product fermentor facility. This invention also relates to the use of mixed cultures in a fermentor.

2. Description of Related Art

The potential for genetic markers in yeast strain identification has been recognized, and deliberately marked enological strains were developed by Vezinhet and Lacroix, *Bull, O.I.V.*, 643–644, 759–773 (1984). Petering et al., *Am. J. Enol. Vitic.*, 42: 6 (1991) discloses a procedure which utilizes recombinant DNA technology to introduce the *E. coli* β-glucuronidase (GUS) gene as a marker into any desired yeast strain. Manufacture of new strains of microorganisms, which is applicable to microorganisms in which reproduction is normally asexual, is described in U.S. Pat. No. 2,820,742. The role of luciferase, along with its uses in luminescent assays and as a marker gene were reviewed by Ugarova et al., *Biokhimiya*, 58: 1351–1372 (1993). The luciferase gene can be inserted into contaminating bacteria using bacteriophages, and luciferase genes can be used as a marker in recombinant DNA studies, to assay promoter, and for other activities. Prosser et al., *Critical Reviews in Biotechnology*, 16: 157–183 (1996) discloses the development of techniques for detecting and tracking microorganisms in natural environments, and the development of molecular marker systems for such studies. In enology, the problem is to discriminate one strain from a huge variety of potential contaminants. Two approaches can be used: the use of an acquired characteristic, and genetic implantation of a discriminatory and easily localized property. The first is poorly suitable to vinification. The genetic labeling described in the above paper consists in the acquisition of antibiotic resistance (chloramphenicol and oligomycin) by the strain. Genetic determinism of this resistance is located in the cell mitochondrial genome. The labeling has the following characteristics: the nuclear genome is not modified; thus the risk of modifying the enologic potential of the strain is minimal, the acquired characteristics are easily recognized (growth on specific media), and no selective disadvantage is in natural competition for the labeled strain.

The advent of biotechnology has led to the clinical use and subsequent approval in the United States alone of more than ten recombinantly produced proteins, including gamma-interferon, beta-interferon, alpha-interferon, insulin, Factor VIII, tissue plasminogen activator, human growth hormone, colony stimulating factors, erythropoietin, and DNase. In addition, there are many drugs being developed or in the clinic for future approval. Capacity is limited in fermentation facilities, so that the same fermentor must be used for making different products. One-example is making different antibodies in the same fermentor. Similarly, an adjacent fermentor may simultaneously be producing a different product. For measures used to prevent the cross-contamination of licensed biological products manufactured in a multiuse facility and regulatory issues involved when facilities are used to manufacture more than one product, see Bader et al., "Multiuse Manufacturing Facilities for Biologicals," *BioPharm*, 5: 32–40 (September 1992).

There is a clear need for being able to detect whenever organisms producing a different product have contaminated the desired production culture. In a multiple-product facility, the contaminant could be any of several very similar organisms. The test must be simple to conduct and must sensitively detect any of the potential contaminants.

SUMMARY OF THE INVENTION

In one embodiment, this invention provides an assay for determining the presence of contaminating microbial host cells in a culturing vessel containing a microbial host cell strain that utilizes more than one carbohydrate source as substrate comprising:

(a) culturing the microbial host cell strain in the vessel, wherein the strain comprises nucleic acid encoding a polypeptide of interest and is genetically marked so as not to utilize a carbohydrate source as a substrate;

(b) plating an isolated sample of culture from step (a) onto culture media supplemented with a carbohydrate source not utilized by the host cell strain as a substrate;

(c) incubating the plated cells at a temperature and for a time sufficient for any positive colony to grow to a detectable level; and (d) detecting whether any colonies are growing on the supplemented culture media.

Furthermore, the invention provides an assay for identifying contaminating microbial host cells in a culturing vessel containing a microbial host cell strain that utilizes more than one carbohydrate source as a substrate, wherein any contaminating microbial host cells and the microbial host cell strain are uniquely genetically marked by their specific carbohydrate utilization characteristics, comprising:

(a) culturing the microbial host cell strain in the vessel, which strain comprises nucleic acid encoding a polypeptide of interest and is genetically marked so as not to utilize a carbohydrate source as a substrate;

(b) plating an isolated sample of culture from step (a) onto culture media supplemented with a carbohydrate source not utilized by the host cell strain as a substrate;

(c) incubating the plated cells at a temperature and for a time sufficient for any positive colony to grow to a detectable level;

(d) detecting whether any colonies are growing on the supplemented culture media;

(e) recovering from the supplemented culture media any colonies growing thereon; and (f) plating the recovered colonies on a field of different carbohydrates to identify any contaminating host cells by their specific carbohydrate utilization characteristics. Typically, in this assay a contaminant protein product is identified by virtue of identifying the contaminating host cells. Each production organism needing introduction to the facility would be genetically marked by a unique marker or combination of markers.

In another embodiment, the invention supplies a process for producing, in a single culturing vessel, multiple polypeptides of interest from microbial host cell strains that utilize more than one carbohydrate source as a substrate, which process comprises:

(a) culturing in the vessel a first microbial host cell strain which comprises nucleic acid encoding a first polypeptide of interest and which is genetically marked so as not to use a first carbohydrate source as a substrate;

(b) plating an isolated sample of culture from step (a) onto culture media supplemented with a carbohydrate source not utilized by the host cell strain;

(c) incubating the plated cells at a temperature and for a time sufficient for any positive colony to grow to a detectable level;

(d) detecting whether any colonies are growing on the supplemented culture media;

(e) after culturing of the first microbial host cell strain is complete, removing the contents of the culturing vessel and cleaning and sterilizing the vessel;

(f) culturing in the vessel a second microbial host cell strain which comprises nucleic acid encoding a second polypeptide of interest and which is genetically marked so as not to use a second carbohydrate source as a substrate, wherein the strain can use the first carbohydrate source as a substrate;

(g) plating an isolated sample of culture from step (f) onto culture media supplemented with a carbohydrate source not utilized by the second host cell strain;

(h) incubating the plated cells at a temperature and for a time sufficient for any positive colony to grow to a detectable level; and (i) detecting whether any colonies are growing on the supplemented culture media to determine if there is contamination from the first host cell strain.

In a still further embodiment, the invention provides a process for conducting, in a single culturing vessel, mixed culturing of microbial host cell strains that utilize more than one carbohydrate source as a substrate, which process comprises:

(a) culturing in the vessel the microbial host cell strains, all of which are genetically marked so as not to utilize a set of n–1 carbohydrate sources as substrates, where n is the number of microbial host cell strains, which set of carbohydrate sources is different for each genetic marking employed;

(b) diluting an isolated sample of culture until a countable number of viable cells will be present when the sample is plated;

(c) plating the diluted sample of culture onto culture media supplemented with a carbohydrate source only utilized by one of the host cell strains as a substrate;

(d) incubating the plated cells at a temperature and for a time sufficient for any positive colony to grow to a detectable level; and (e) comparing growth or cell population changes of the different strains by enumerating the colonies growing on the supplemented culture media and comparing the number of colonies on each of the carbohydrate sources.

There are several features of this test which make it attractive. It is a simple test which can be very sensitive in recognizing unwanted, foreign microorganisms. The sensitivity can also be adjusted to accommodate features of the marker mutations used. There are a large number of hosts that could be marked since, for example, $E.\ coli$ can utilize a wide range of carbon sources. The number of false positives is low, especially when deletion mutations are utilized.

In addition, GMP production has been limited in the past because cross-product contamination events could not be detected. Hence, if even a slight breach in total containment occurred, the whole fermentation batch had to be discarded to avoid risking an unacceptable level of cross-product contamination. This invention allows measurement of previously undetectable quantities of cross-host contaminants, so that it can be determined whether the contaminant levels are within acceptable limits and hence whether the batch needs to be disposed of. This avoids unnecessarily discarding batches that may have been within allowable limits but could not be assessed definitively as being acceptable.

DETAILED DESCRIPTION OF THE PREFERRED EMBODIMENTS

Definitions

As used herein, "contaminating" cells and "contaminants" are those materials that are not desirable to be present in a particular culture of interest.

For purposes herein, "culturing vessel" is a vessel that is used to culture the microbial host cell strain(s). This would include shaker flasks as well as fermentors such as those intended for large-scale production of polypeptide. The fermentor is suitably any size, including 1-L, 10-L, 1000-L, 10,000-L and 100,000-L tanks.

As used herein, "polypeptide" or "polypeptide of interest" refers generally to peptides and proteins having more than about ten amino acids. Preferably, the polypeptides are "exogenous," meaning that they are "heterologous," i.e., foreign to the host cell being utilized, such as a human protein produced by $E.\ coli$.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; $\alpha$1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-$\beta$; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The preferred exogenous polypeptides of interest are mammalian polypeptides. Examples of such mammalian polypeptides include enzymes, hormones, cytokines, chemokines, immunotoxins, viral components, antibodies, neurotrophins, and antigens. Suitable such proteins encompass human polypeptides such as t-PA, gp120, anti-CD11a, anti-CD18, anti-VEGF, VEGF, TGF-beta, activin, inhibin, anti-HER-2, DNase, IGF-I, IGF-II, brain IGF-I, growth hormone, relaxin chains, growth hormone releasing factor, insulin chains or pro-insulin, NGF, NT-3, BDNF, and urokinase. Particularly preferred mammalian polypeptides include, e.g., t-PA, gp120(IIIb), anti-HER-2, anti-CD11a, anti-CD18, anti-VEGF, VEGF, DNase, IGF-I, IGF-II, TGF-beta, IGFBP-3, IGFBP-2, IGFBP-1, growth hormone, NGF, NT-3, NT-4, NT-5, and NT-6. The polypeptide is more preferably IGF, most preferably IGF-I.

As used herein, "IGF-I" refers to insulin-like growth factor from any species, including bovine, ovine, porcine, equine, and preferably human, in native sequence or in variant form and recombinantly produced. In a preferred method, the IGF-I is cloned and its DNA expressed in bacteria, e.g., by the process described in EP 128,733 published Dec. 19, 1984.

As used herein, "genetically marked" means having one or more genetic markers, or chromosomal markers, which cause the strain in which the marker(s) is/are present not to use a carbohydrate source as a substrate.

The expression "carbohydrate source" means any source of a carbohydrate, including, for example, ribose, xylose, mannose, maltose, glucose, sucrose, fucose, fructose, lactose, and rhamnose. Preferably, the carbohydrate source herein is not one that is used in conjunction with inducing a promoter for production of the host cell strain, such as lactose or arabinose. Most preferably, the carbohydrate source is maltose, ribose, fucose, or rhamnose.

"Carbohydrate utilization revertants or suppressors" are defined as those mutated strains that have reverted back to their non-mutated state or have acquired a suppressor mutation at another site, typically by spontaneous modification of the host organism. For reverting genotypes, the gene that is mutated in the strain involves a carbohydrate utilization pathway that has the capability of reverting the gene to its wild-type form. A "non-reverting" alteration is a genetic alteration that does not cause the strain to revert back to its non-mutated state. A "non-suppressing" alteration is one in which the organism does not acquire a suppressor mutation at another site.

"Microbial host cell strains that utilize more than one carbohydrate source as a substrate" are those microorganisms that have the normal, or native, capability of utilizing two or more carbohydrates as substrates, such as most bacteria and at least some fungi and yeast, including, without limitation, Aspergillus, Saccharomyces, Schizosaccharomyces, Candida, Kluyveromyces, and Pichia, more preferably A. awamori, S. cerevisiae, S. dairensis, Schizosaccharomyces pombe, K. marxianus, K. thermotolerans, C. albicans, C. anatomiae, and P. pastoris.

A "sample" of culture is a small portion of the cell culture taken to conduct the assay herein.

The expression "control sequences" refers to DNA sequences necessary for the expression of an operably linked coding sequence in a particular host organism. The control sequences that are suitable for microorganisms include a promoter such as the alkaline phosphatase promoter for bacteria, optionally an operator sequence, and a ribosome-binding site.

Nucleic acid is "operably linked" when it is placed into a functional relationship with another nucleic acid sequence. For example, DNA for a presequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The technique of "polymerase chain reaction," or "PCR," as used herein generally refers to a procedure wherein minute amounts of a specific piece of nucleic acid, RNA, and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5'-terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., *PCR Technology*, (Stockton Press, NY, 1989). For a recent review on PCR advances, see Erlich et al., *Science*, 252: 1643–1650 (1991).

As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Minimal media" refers to culture media designed for plates having the minimum amount of media ingredients necessary to grow colonies of cells. Typically, such media is minimal agar media. One example is media containing, per liter, about 0.1–0.2 g $MgSO_4$ heptahydrate, about 15 g Bacto-agar, about 10 mM $NH_4Cl$, about 10–12 g $K_2HPO_4$, about 4–5 g $KH_2PO_4$, and about 0.5 g sodium citrate dihydrate.

Modes for Carrying Out the Invention

The assay of this invention comprises a multi-step procedure for identifying contaminating microorganisms in a culture. In the first step, a microbial host cell strain that utilizes more than one carbohydrate source as defined above is cultured in culture medium in a suitable vessel for growing up the cells. This strain contains nucleic acid encoding the polypeptide desired to be produced. It also is genetically marked such that the strain does not use a carbohydrate source as a substrate.

Fermentation parameters are used and polypeptide production is conducted in a conventional manner, such as those procedures described below. During the process for production of the polypeptide of interest, the genetic marker(s), if a mutation or alteration, is/are silent, since the microorganism does not encounter the carbohydrate during the fermentation process.

I. Fermentation

A. Insertion of Nucleic Acid into a Replicable Vector

The nucleic acid encoding the polypeptide of interest is suitably cDNA or genomic DNA from any source, provided it encodes the polypeptide(s) of interest, and is generally the native sequence.

The heterologous nucleic acid (e.g., cDNA or genomic DNA) is suitably inserted into a replicable vector for expression in the microorganism under the control of a suitable promoter. Many vectors are available for this purpose, and selection of the appropriate vector will depend mainly on the size of the nucleic acid to be inserted into the vector and the particular host cell to be transformed with the vector. Each vector contains various components depending on the particular host cell with which it is compatible. Depending on the particular type of host, the vector components generally include, but are not limited to, one or more of the following: a signal sequence, an origin of replication, one or more marker genes, a promoter, and a transcription termination sequence.

In general, plasmid vectors containing replicon and control sequences that are derived from species compatible with the host cell are used in connection with microbial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 [1977]). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

(i) Signal Sequence Component

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell.

For prokaryotic host cells that do not recognize and process the native polypeptide signal sequence, the signal sequence is substituted by a prokaryotic signal sequence selected, for example, from the group consisting of the alkaline phosphatase, penicillinase, lpp, or heat-stable enterotoxin II leaders. For yeast secretion the native signal sequence may be substituted by, e.g., the yeast invertase, alpha factor, or acid phosphatase leaders, the *C. albicans* glucoamylase leader (EP 362,179 published Apr. 4, 1990), or the signal described in WO 90/13646 published Nov. 15, 1990.

(ii) Origin of Replication Component

Expression vectors contain a nucleic acid sequence that enables the vector to replicate in one or more selected host cells. Such sequences are well known for a variety of bacteria and yeast. The origin of replication from the plasmid pBR322 is suitable for most Gram-negative bacteria, and the $2\mu$ plasmid origin is suitable for yeast.

(iii) Selection Gene Component

Expression vectors generally contain a selection gene, also termed a selectable marker. This gene encodes a protein necessary for the survival or growth of transformed host cells grown in a selective culture medium. Host cells not transformed with the vector containing the selection gene will not survive in the culture medium. This selectable marker is separate from the genetic markers as utilized and defined by this invention. Typical selection genes encode proteins that (a) confer resistance to antibiotics or other toxins, e.g., ampicillin, neomycin, methotrexate, or tetracycline, (b) complement auxotrophic deficiencies other than those caused by the presence of the genetic marker(s), or (c) supply critical nutrients not available from complex media, e.g., the gene encoding D-alanine racemase for Bacilli.

One example of a selection scheme utilizes a drug to arrest growth of a host cell. In this case, those cells that are successfully transformed with the nucleic acid of interest produce a polypeptide conferring drug resistance and thus survive the selection regimen. Examples of such dominant selection use the drugs neomycin (Southern et al., *J. Molec. Appl. Genet.*, 1: 327 [1982]), mycophenolic acid (Mulligan et al., *Science*, 209: 1422 [1980]) or hygromycin (Sugden et al., *Mol. Cell. Biol.*, 5: 410–413 [1985]). The three examples given above employ bacterial genes under eukaryotic control to convey resistance to the appropriate drug G418 or neomycin (geneticin), xgpt (mycophenolic acid), or hygromycin, respectively.

A suitable selection gene for use in yeast is the trp1 gene present in the yeast plasmid YRp7 (Stinchcomb et al., *Nature*, 282: 39 [1979]; Kingsman et al., *Gene*, 7: 141 [1979]; or Tschemper et al., *Gene*, 10: 157 [1980]). The trp1 gene provides a selection marker for a mutant strain of yeast lacking the ability to grow in tryptophan, for example, ATCC No. 44076 or PEP4-1 (Jones, *Genetics*, 85: 12 [1977]). The presence of the trp1 lesion in the yeast host cell genome then provides an effective environment for detecting transformation by growth in the absence of tryptophan. Similarly, leu2 deficient yeast strains (ATCC 20,622 or 38,626) are complemented by known plasmids bearing the leu2 gene.

(iv) Promoter Component

The expression vector for producing the polypeptide of interest contains a suitable promoter that is recognized by the host microbial organism and is operably linked to the nucleic acid encoding the polypeptide of interest. Promoters suitable for use with prokaryotic hosts include the β-lactamase and lactose promoter systems (Chang et al., *Nature*, 275: 615 [1978]; Goeddel et al., *Nature*, 281: 544 [1979]), the arabinose promoter system (Guzman et al., *J. Bacteriol.*, 174: 7716–7728 [1992]), alkaline phosphatase, a tryptophan (trp) promoter system (Goeddel, *Nucleic Acids Res.*, 8: 4057 [1980] and EP 36,776) and hybrid promoters such as the tac promoter (deBoer et al., *Proc. Natl. Acad. Sci. USA*, 80: 21–25 [1983]). However, other known bacterial promoters are suitable. Their nucleotide sequences have been published, thereby enabling a skilled worker operably to ligate them to DNA encoding the polypeptide of interest (Siebenlist et al., *Cell*, 20: 269 [1980]) using linkers or adaptors to supply any required restriction sites.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

Promoter sequences are known for eukaryotes such as yeast and fungi. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; and Holland, *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A.

Yeast enhancers also are advantageously used with yeast promoters. See, for example, Yaniv, *Nature*, 297: 17–18 (1982) on enhancing elements for activation of eukaryotic promoters. The enhancer may be spliced into the vector at a position 5' or 3' to the polypeptide-encoding sequence, but is preferably located at a site 5' from the promoter.

(v) Transcription Termination Component

Expression vectors used in eukaryotic host cells including yeast and fungi will also contain sequences necessary for the termination of transcription and for stabilizing the mRNA. Such sequences are commonly available from the 5' and, occasionally 3' untranslated regions of eukaryotic or viral DNAs or cDNAs.

(vi) Construction and Analysis of Vectors

Construction of suitable vectors containing one or more of the above listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., *Proc. Natl. Acad. Sci. USA*, 74: 5463–5467 (1977) or Messing et al., *Nucleic Acids Res.*, 9: 309 (1981), or by the method of Maxam et al., *Methods in Enzymology*, 65: 499 (1980).

B. Selection and Transformation of Host Cells

Suitable microbial host cells for expressing the vectors herein are the prokaryote, yeast, and fungi provided they meet the criteria noted above for carbohydrate utilization and are genetically marked as defined herein. Suitable prokaryotes include bacteria such as archaebacteria and eubacteria, encompassing Gram-negative or Gram-positive organisms. Preferred bacteria for this purpose are eubacteria, and more preferably Enterobacteriaceae. Examples of useful bacteria include those from the species Escherichia, Enterobacter, Azotobacter, Erwinia, Bacillus, Pseudomonas, Klebsiella, Proteus, Salmonella, Serratia, Shigella, Rhizobia, Vitreoscilla, and Paracoccus, e.g., *E. coli, B. subtilis, P. aeruginosa, S. typhimurium,* or *Serratia marcescans.*

*E. coli* hosts suitable as starting hosts to be marked include *E. coli* W3110 (ATCC 27,325), *E. coli* 294 (ATCC 31,446), *E. coli* B, and *E. coli* X1776 (ATCC 31,537). These examples are illustrative rather than limiting. Mutant cells of any of the above-mentioned bacteria may also be employed as the starting hosts that are then marked. It is, of course, necessary to select the appropriate bacteria taking into consideration replicability of the replicon in the cells of a bacterium. For example, *E. coli,* Serratia, or Salmonella species can be suitably used as the host when well known plasmids such as pBR322, pBR325, pACYC177, or pKN410 are used to supply the replicon.

*E. coli* strain W3110 is a preferred host to be genetically marked because it is a common host strain for recombinant DNA product fermentations. Preferably, the host cell should secrete minimal amounts of proteolytic enzymes. Examples of starting bacterial hosts to be marked, along with their genotypes, are included in the table below:

| Strain | Genotype |
| --- | --- |
| W3110 | K-12 F⁻ lambda⁻ IN(rrnD-rrnE)1 |
| 1A2 | W3110 ΔfhuA |
| 9E4 | W3110 ΔfhuA ptr3 |
| 27A7 | W3110 ΔfhuA ptr3 phoAΔE15 Δ(argF-lac)169 |
| 27C6 | W3110 ΔfhuA ptr3 phoAΔE15 Δ(argF-lac)169 ΔompT |
| 27C7 | W3110 ΔfhuA ptr3 phoAΔE15 Δ(argF-lac)169 ΔompT degP41 (ΔpstI-kan$^R$) |
| 33D3 | W3110 ΔfhuA ptr3 lacIq lacL8 ΔompT degP41 (ΔpstI-kan$^R$) |
| 36F8 | W3110 ΔfhuA phoAΔE15 Δ(argF-lac)169 ptr3 degP41 (ΔpstI-kan$^R$) ilvG2096$^R$ |
| 43D3 | W3110 ΔfhuA ptr3 phoAΔE15 Δ(argF-lac)169 ΔompT degP41 (ΔPst1-kan$^R$) ilvG2096$^R$ |
| 43E7 | W3110 ΔfhuA Δ(argF-lac)169 ΔompT ptr3 phoAΔE15 degP41 (ΔPst1-kan$^S$) ilvG2096$^R$ |
| 44D6 | W3110 ΔfhuA ptr3 Δ(argF-lac)169 degP41 (Δpst1-kan$^S$) ΔompT ilvG2096$^R$ |
| 45F8 | W3110 ΔfhuA ptr3 Δ(argF-lac)169 degP41 (Δpst1-kan$^S$) ΔompT phoS* (T10Y) ilvG2096$^R$ |
| 45F9 | W3110 ΔfhuA ptr3 Δ(argF-lac)169 degP41 (Δpst1-kan$^S$) ΔompT ilvG2096$^R$ phoS* (T10Y) Δcyo::kan$^R$ |

Also suitable are the intermediates in making strain 36F8, 27B4 (U.S. Pat. No. 5,304,472) and 35E7 (a spontaneous temperature-resistant colony isolate growing better than 27B4), as well as the intermediate in making strain 48A4, strain 46H9 described in Example III below. An additional suitable strain is the *E. coli* strain having the mutant periplasmic protease(s) disclosed in U.S. Pat. No. 4,946,783 issued Aug. 7, 1990.

In addition to prokaryotes, eukaryotic microbes such as filamentous fungi or yeast are suitable hosts herein provided they meet the carbohydrate utilization criteria. *Saccharomyces cerevisiae,* or common baker's yeast, is the most commonly used among lower eukaryotic host microorganisms. However, a number of other genera, species, and strains are commonly available and useful herein, such as *Saccharomyces dairensis; Schizosaccharomyces pombe* [Beach and Nurse, *Nature,* 290: 140 (1981); EP 139,383 published May 2, 1985]; Kluyveromyces hosts (U.S. Pat. No. 4,943,529) such as, e.g., *K. lactis* [Louvencourt et al., *J. Bacteriol.*, 737 (1983)], *K. fragilis, K. bulgaricus, K. thermotolerans,* and *K. marxianus;* Yarrowia [EP 402,226]; *Pichia pastoris* [EP 183,070; Sreekrishna et al., *J. Basic Microbiol.*, 28: 265–278 (1988)]; Candida hosts such as, e.g., *Candida albicans* and *Candida anatomiae; Trichoderma reesia* [EP 244,234]; *Neurospora crassa* [Case et al., *Proc. Natl. Acad. Sci. USA*, 76: 5259–5263 (1979)]; and filamentous fungi such as, e.g, Neurospora, Penicillium, Tolypocladium [WO 91/00357 published Jan. 10, 1991], and Aspergillus hosts such as *A. nidulans* [Ballance et al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)] and *A. niger* [Kelly and Hynes, *EMBO J.*, 4: 475–479 (1985)].

In a preferred facet of this invention, the genetic marker is created by altering the genotype of the strain. This alteration may be non-reverting and/or non-suppressing, reverting or suppressing, or a combination thereof. In addition, the strain is suitably marked multiple times. The ability of the strain to have more than one genetic marker can be advantageous in allowing a larger collection of hosts to be employed. The multiply marked strain may contain alterations in two or more different carbohydrate utilization pathways, utilizing, for example, pathway enzymes, transport components, and regulatory components.

If two different carbohydrate utilization pathways are used, the strain may be marked with one non-reverting, non-suppressing mutation and one reverting or suppressing mutation. One example is where the non-reverting mutation is in ribose utilization and the reverting mutation is a point mutation in rhamnose utilization, such as a $\Delta$(rbs7) mutation and a rhaR mutation.

The strain may also be marked with two non-reverting (and non-suppressing) carbohydrate mutations. For example, one non-reverting mutation is in maltose utilization and the other non-reverting mutation is in ribose utilization, such as a $\Delta$(malE) mutation and a $\Delta$(rbs7) mutation.

The total number of independent marked strains (TMS) that can be derived is a function of the total number of markers (TM) and the number of markers per strain (MPS) as set forth in the following equation:

$$TMS = (TM)! / (MPS)! \, (TM-MPS)!$$

Thus, with two markers per strain, the total number of independent marked strains is:

| No. of markers:       | 2 | 3 | 4 | 5  | 6  | 7  |
|-----------------------|---|---|---|----|----|----|
| No. of marked strains:| 1 | 3 | 6 | 10 | 15 | 21 |

With three markers per strain, the total number of independent marked strains is:

| No. of markers:       | 3 | 4 | 5  | 6  | 7  |
|-----------------------|---|---|----|----|----|
| No. of marked strains:| 1 | 4 | 10 | 20 | 35 |

Thus, there must be a need for more than ten marked strains before it is worth inserting three markers into each strain.

Examples of marked bacterial strains that are suitable herein are indicated in the table below.

| | |
|---|---|
| 37D6 | W3110 $\Delta$fhuA ptr3 phoA$\Delta$E15 $\Delta$(argF-lac)169 $\Delta$ompT degP41 ($\Delta$pst1-kan$^R$) $\Delta$(rbs7) ilvG2096$^R$ |
| 40B4 | W3110 $\Delta$fhuA ptr3 phoA$\Delta$E15 $\Delta$(argF-lac)169 $\Delta$ompT degP41 ($\Delta$pst1-kan$^S$) $\Delta$(rbs7) ilvG2096$^R$ |
| 46F1 | W3110 $\Delta$fhuA ptr3 $\Delta$(argF-lac)169 degP41 ($\Delta$pst1-kan$^S$) $\Delta$ompT ilvG2096$^R$ phoS* (T10Y) $\Delta$cyo::kan$^R$ rhaR |
| 46D5 | W3110 $\Delta$fhuA ptr3 $\Delta$(argF-lac)169 degP41 ($\Delta$pst1-kan$^S$) $\Delta$ompT ilvG2096$^R$ phoS* (T10Y) $\Delta$cyo::kan$^R$ rhaR $\Delta$(rbs7) |
| 48A4 | W3110 $\Delta$fhuA $\Delta$malE $\Delta$(rbs7) |

Of those given above, the preferred strains are 46D5 and 48A4.

The nucleic acid encoding the polypeptide is inserted into the host cells. Preferably, this is accomplished by transfecting, and preferably transforming, the host cells with the above-described expression vectors and culturing in conventional nutrient media modified as appropriate for inducing the various promoters.

Transfection refers to the taking up of an expression vector by a host cell whether or not any coding sequences are in fact expressed. The term "transfection" includes such techniques as transformation, conjugation, and transduction. Numerous methods of transfection are known to the ordinarily skilled artisan, for example, $CaPO_4$ and electroporation as well as transformation methods described below. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* [New York: Cold Spring Harbor Laboratory Press, 1989], is generally used for prokaryotic cells or other cells that contain substantial cell-wall barriers. Another method for transformation employs polyethylene glycol/DMSO, as described in Chung and Miller, *Nucleic Acids Res.*, 16: 3580 (1988). Yet another method is the use of the technique termed electroporation. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979).

C. Culturing the Host Cells

Prokaryotic cells used to produce the polypeptide of interest are cultured in suitable media as described generally in Sambrook et al., supra. The culture conditions, such as temperature, pH, and the like, are those previously used with the host cell selected for expression, and will be apparent to the ordinarily skilled artisan.

Where the alkaline phosphatase promoter is employed, bacterial cells used to produce the polypeptide of interest of this invention are cultured in suitable media in which the alkaline phosphatase promoter can be partially or completely induced as described generally, e.g., in Sambrook et al., supra. The culturing need never take place in the absence of inorganic phosphate or at phosphate starvation levels. At first, the medium contains inorganic phosphate in an amount above the level of induction of protein synthesis and sufficient for the growth of the bacterium. As the cells grow and utilize phosphate, they decrease the level of phosphate in the medium, thereby causing induction of synthesis of the polypeptide.

Any other necessary media ingredients besides carbon, nitrogen, and inorganic phosphate sources may also be included at appropriate concentrations introduced alone or as a mixture with another ingredient or medium such as a complex nitrogen source. The pH of the medium may be any pH from about 5–9, depending mainly on the host organism.

If the promoter is an inducible promoter, for induction to occur, typically the cells are cultured until a certain optical density is achieved, e.g., a $A_{550}$ of about 60–80, at which point induction is initiated (e.g., by addition of an inducer, by depletion of a medium component, etc.), to induce expression of the gene encoding the polypeptide of interest.

D. Detecting Expression

Gene expression may be measured in a sample directly, for example, by conventional Southern blotting, northern blotting to quantitate the transcription of mRNA (Thomas, *Proc. Natl. Acad. Sci. USA,* 77: 5201–5205 [1980]), dot blotting (DNA analysis), or in situ hybridization, using an appropriately labeled probe, based on the sequences of the polypeptide. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, assays or gels may be employed for detection of protein.

For secretion of an expressed gene product, the host cell is cultured under conditions sufficient for secretion of the gene product. Such conditions include, e.g., temperature, nutrient, and cell density conditions that permit secretion by the cell. Moreover, such conditions are those under which the cell can perform basic cellular functions of transcription, translation, and passage of proteins from one cellular compartment to another, as are known to those skilled in the art.

II. Assay

In the application of this assay, one obtains a sample from the microbial fermentation culture. If the culture is a high-density fermentation culture, the sample preferably contains about $10^8$ to $10^{10}$ colony forming units (CFU) per ml of culture. Typically, this sample is taken at the end of the fermentation, but it can be taken at any time during culturing. The cells from the isolated sample are plated on one or more plates having culture media supplemented with one of the carbohydrate sources not utilized by the marked host. Preferably two plates are employed, each one supplemented with one of the carbohydrate sources not utilized by the marked host. In another preferred embodiment, the plates are minimal media plates, most preferably minimal agar plates.

If a high-density fermentor is used as the culture vessel, depending mainly on the type of genetic marking on the host cell strain, cells are plated either directly (preferably about $10^8$ to $10^{11}$ CFU/ml of culture) or diluted to a level sufficient to avoid detection of carbohydrate utilization revertants or suppressors, and applied to the plate(s). If the cells are diluted, preferably they are serially diluted, starting with about $10^8$ to $10^{11}$ CFU/ml of culture and ending with about $10^5$ to $10^8$ CFU/ml of culture, in, for example, culture media or phosphate-buffered saline (PBS). An example of when dilution is indicated is when the marker mutation is a reverting mutation or can be suppressed, e.g., by a spontaneous modification of the host organism, so as to create, or result in, a carbohydrate utilization revertant or suppressor. The dilution is done to ensure that the reversion or suppression of the marker mutation does not interfere with the results (false positives). Dilution of the sample such that about $10^6$ colony forming units per ml are plated gives a satisfactory level of sensitivity with an adequate margin of safety for elimination of false positive results. Another reason for diluting is simply to reduce the sensitivity of the test, if desired.

The culture media on the plates can be augmented individually or in combination with amino acids, trace elements, vitamins, or nucleotide bases in a concentration to allow for growth of any auxotrophic strains which are desired to be detected. Any ingredient which could be used as a sole carbon source by a bacterium such as *E. coli* should be added at sufficiently low concentration that it does not enable colony formation of the marked strain.

Then, the plate(s) are incubated at a suitable temperature and for a suitable time to allow a positive colony to grow sufficiently for detection, i.e., reliable, accurate detection. The period of time necessary for incubation will depend, for example, on the temperature of incubation, the type of marker, and the type of microbial strain. Typically, the temperature ranges from about 20 to 40° C., more preferably about 30–38° C., and most preferably about 37° C.; and the time for incubation ranges from about 24 to 120 hours, more preferably about 35–90 hours if the temperature is about 30–38° C., most preferably about 48–72 hours if the temperature is about 37° C.

Finally, a detection step is employed to determine whether any colonies are growing on the plate(s). The presence of colonies, determined readily by visual inspection, indicates the presence of contaminating microbial strains, since they would grow on the carbohydrate source with which the plate(s) were supplemented. Within the guidelines set forth above regarding the CFUs of the sample upon plating, the sensitivity of the test is detection of approximately 1 in $10^6$ to 1 in $10^{10}$ cross-host contaminating organisms.

As a further step, any colonies detected can be identified as being from the microbial host cell strain that was cultured or another strain. For example, if the desired host strain is an *E. coli,* these organisms could be further identified as *E. coli* or non-*E. coli* contaminants. If the colonies are from an *E. coli* host strain, one can identify which host strain by its unique carbohydrate utilization capacity. Therefore, one can identify which contaminating polypeptide, presumably heterologous polypeptide, must be separated from the desired product, since the polypeptide will be produced from the contaminating strain and hence associated or identified with it.

In one aspect of this identification process, after the detecting step any colonies growing on the supplemented culture media are recovered or removed from the supplemented culture media and plated on a field or survey of various types of carbohydrate sources to identify any contaminating host cells by their specific, unique carbohydrate utilization deficiencies.

The assay herein is also particularly useful in a process for manufacturing multiple polypeptides in a single culturing vessel or in a single facility so that residual host cells producing one type of polypeptide do not contaminate a host cell culture producing another type of polypeptide. The assay is carried out as described above through the detection step. If any positive colonies are growing on the plate(s), the operator would then determine whether the batch needs to be discarded or can continue to be used. After the first microbial host cell strain is cultured to completion, the contents of the culturing vessel are emptied, and the vessel is cleaned and sterilized. Then, a second microbial host cell strain is introduced into and cultured in the same or an adjacent culturing vessel. This second strain contains nucleic acid encoding a second polypeptide and is genetically marked by a different marker or markers than used in the culturing of the first strain. Such marker(s) causes the strain not to use a different carbohydrate source as a substrate. This second strain is able to use the first carbohydrate source as a substrate.

The process for making more than one polypeptide in the same fermentor further comprises the steps of isolating and plating a sample of the second-polypeptide-producing cell culture onto culture media supplemented with a carbohydrate source not utilized by the second host cell strain; incubating the plate(s) at a temperature and for a time sufficient for any positive colony(ies) to grow to full size; and detecting whether any colonies are growing on the plate(s). These steps are all conducted as described above. After the culturing vessel is emptied, cleaned, and sterilized, the above steps, starting with the culturing step, may be repeated indefinitely using a third or higher number of strain that will not use a third carbohydrate source as a substrate, but is able to use the first and second carbohydrate sources as substrates, all sources being different.

In another facet of the invention, mixed culturing in a single culturing vessel can be carried out. This would be useful, for example, in waste treatment where more than one organism is required to adequately remove potential pollutants. For example, U.S. Pat. No. 5,543,324 describes microbially mediated degradation of nitrogen-containing phenol compounds. This degradation utilizes a consortium of microorganisms comprising the bacterial genera Arthrobacter, Aurobacterium, and Pseudomonas. The consortium is isolated from waste treatment sludge and is capable of completely degrading picric acid.

Alternatively, this mixed culturing aspect can be used easily to assess different cell population changes and comparative growth in a culture medium. This process involves the following steps.

First, more than one microbial host cell strain is cultured in a single culturing vessel. One or more of these strains may, but need not, comprise nucleic acid encoding a polypeptide of interest. All of them are genetically marked so as not to utilize a set of n−1 carbohydrate sources as substrates, where n is the number of microbial host cell strains. The set of carbohydrate sources is different for each genetic marking employed.

After the culturing step, an isolated sample of culture is diluted such that a limited number of growing colonies (a number able to be counted) will appear on each plate when the sample is plated, so that the colonies are not too numerous to be counted. Dilution can be with the culture media employed in the culturing step or other suitable diluent for growing the cells. The countable number of colonies is typically about 10–200 cells per plate.

Once dilution is achieved, the sample is plated onto culture media supplemented with a carbohydrate source only utilized by one of the host cell strains as a substrate. Hence, for example, a 0.1 ml sample of culture is isolated and diluted to 1 ml so that 10–200 of viable colonies will be present. This 1-ml sample is then plated as described above. The plated cells are incubated at a temperature and for a time sufficient for any positive colony to grow to a detectable level. After this step the growth or cell population changes of the different strains are compared by enumerating, i.e., counting the number of, the colonies growing on the supplemented culture media and by comparing the number of colonies on each of the carbohydrate sources.

The following examples are offered by way of illustration and not by way of limitation. The disclosures of all patent and scientific references cited in the specification are expressly incorporated herein by reference.

III. EXAMPLES

Construction of Strains

Genetically tagged strains were constructed by introducing into the host a deletion mutation in a carbohydrate utilization pathway. Deletion mutations were (1) constructed by PCR in vitro and recombined into the chromosome, or (2) obtained from an outside source and introduced into the *E. coli* host by P1 transduction. The gene deletions constructed by PCR were created by using oligonucleotides to generate two ends of the gene, removing approximately 500 bp in the internal portion of the gene. The two ends of the gene were ligated together through a SpeI junction. The deletion-containing fragment was subcloned into pS1080. pS1080 has an R6K oriR origin of replication, the multiple cloning site and intergenic region of bacteriophage f1, the β-lactamase gene from PBR322, and the sacB gene from *Bacillus subtilis*. Using M13 transduction and carbenicillin selection, the entire plasmid was recombined into the chromosome of a W3110 derivative that will not support independent replication of the plasmid vector. Subsequent P1 transduction was used to move the deletion plasmid integrated into the chromosome into other *E. coli* host backgrounds using carbenicillin selection. To obtain plasmid resolvants, sucrose-resistant derivatives were selected at room temperature and then screened for loss of carbencillin resistance. Chromosomal DNA from sucrose-resistant carbenicillin-sensitive colonies was confirmed to carry the planned deletion using PCR. The carbohydrate-negative phenotype was also confirmed on MacConkey Agar with 1% of the desired sugar.

Example I

Strain Marked With a Single Non-reverting Carbohydrate Mutation

A sensitive assay for the detection of contaminating organisms in a multi-use manufacturing facility is described in this example. The production organism was marked with a single non-reverting mutation in a carbohydrate utilization pathway. The impact of the mutation was silent in the recombinant protein production stage; however, in subsequent testing the tagged organism could be distinguished by a simple carbohydrate utilization test from other potential cross-contaminating *E. coli* organisms.

Strain 37D6, derived from *E. coli* K-12 W3110, carries a plasmid producing recombinant protein. With genotype W3110 IN(rrnD-rrnE)1 ΔfhuA phoAΔE15 Δ(argF-lac)169 ptr3 degP41 (kan$^R$) ΔompT ilvG2096$^R$ Δ(rbs7), 37D6 is derived from strain 27C7 described in U.S. Pat. No. 5,288,931 and has American Type Culture Collection No. 55,244. The Δ(rbs7) mutation (Lopilato et al., *J. Bacteriol.*, 158: 665–673 [1984]) was introduced by P1 co-transduction so this host could be distinguished from other recombinant hosts by a simple carbohydrate utilization test. The rbs deletion was introduced by P1 co-transduction with a linked Tn10 insertion in the ilv gene. The isoleucine/valine auxotrophy was transduced to prototrophy using P1 phage grown on a strain carrying the ilvG2096$^R$ mutation (Lawther et al., *Proc. Natl. Acad. Sci. USA*, 78: 922–925 [1981]), which repairs a frameshift that causes wild-type *E. coli* K-12 strain to be sensitive to valine. The ribose utilization defect was confirmed as being present in the resulting 37D6 using minimal media containing ribose as a carbon source.

A sample from the end of a 10-L fermentation (performed essentially as described in U.S. Pat. No. 5,288,931) was obtained using aseptic technique and stored at 4° C. prior to plating. Serial 10-fold dilutions into PBS were made. A total of 0.1 ml of sample was plated onto minimal media containing 0.2%–0.4% ribose as a carbon source. The composition of the media contains, per liter: 10 mM NH$_4$Cl; 11.27 grams K$_2$HPO$_4$; 4.83 grams KH$_2$PO$_4$; 0.5 grams sodium citrate dihydrate; 0.123 grams MgSO$_4$ heptahydrate; 15 grams Bacto-agar; and 0.2%–0.4% of the desired carbon source. Plates were incubated at 37° C. for approximately 48–72 hours. This allows sufficient time for a positive colony to grow to a size which is easily detectable. A control culture that could utilize ribose was used to confirm positive growth on this medium.

Colony forming units, i.e., cell population density (CFU/ml), for two fermentations were determined. Fermentation run SI275 had $1.0 \times 10^{10}$ CFU/ml and fermentation run SI276 had $4.0 \times 10^{10}$ CFU/ml. CFU from approximately $10^9$ to $10^4$ per plate were plated. No colonies were observed, as indicated in Table 1. The control culture grew as expected on the ribose plates. These results indicate that the Δ(rbs7) mutation is non-reverting and non-suppressing. Compensatory mutations which might allow for growth on ribose were also not detected. Thus, a culture containing $10^9$ CFU/plate of the desired organism could be plated and the sensitivity of the test with a non-reverting mutation such as this one would be approximately one contaminating organism in $10^9$ cells plated.

TABLE 1

| 37D6 CFU | Colonies Detected |
|---|---|
| Fermentation SI275 | |
| $1 \times 10^9$ | no colonies |
| $1 \times 10^8$ | no colonies |
| $1 \times 10^7$ | no colonies |
| $1 \times 10^6$ | no colonies |
| $1 \times 10^5$ | no colonies |
| $1 \times 10^4$ | no colonies |
| Fermentation SI276 | |
| $4.0 \times 10^9$ | no colonies |
| $4.0 \times 10^8$ | no colonies |
| $4.0 \times 10^7$ | no colonies |
| $4.0 \times 10^6$ | no colonies |
| $4.0 \times 10^5$ | no colonies |
| $4.0 \times 10^4$ | no colonies |

Example II

Multiply Marked Strain With One Non-reverting and One Reverting (Point Mutation) Carbohydrate Mutation To increase the number of production strains that can be marked, the strains can be multiply marked. This example describes the use of doubly marked strains. Each production organism contained mutations in two carbohydrate utilization pathways. In this example the production organism was marked with one non-reverting mutation (ribose utilization) and one reverting mutation (point mutation in rhamnose utilization). Reversion of the point mutation was observed at approximately one revertant in $10^8$ cells plated. In this case, dilution of the production organism to a sufficient level below detection of revertants was preferred. Spiking studies with organisms that can utilize either ribose or rhamnose and ribose indicated that the test is as sensitive as one can expect from the number of spiked organisms plated onto a lawn of the non-utilizing organism.

The strain used in this example was a derivative of *E. coli* K-12 W3110 (carrying a recombinant-protein-producing plasmid).

Strain 46D5, W3110 IN(rrnD-rrnE)1 ΔfhuA Δ(argF-lac) 169 ptr3 degP41 (ΔPstI-kan$^S$) ΔompT phoS*(T10Y) cyo-::kan$^R$ rhaR Δ(rbs7) ilvG2096$^R$ was derived from strain 27C7 (see above) The additional steps in the construction of strain 46D5 are outlined below.

A Tn10 insertion in the ilv gene was introduced into 27C7 by P1 transduction. The isoleucine/valine auxotrophy was transduced to prototrophy using P1 phage grown on a strain carrying the ilvG2096$^R$ mutation (Lawther et al., supra), which repairs a frameshift that causes the wild-type *E. coli* K-12 strain to be sensitive to valine. The resulting strain was 43D3. The ilvG2096$^R$ locus was confirmed by the resistance of the 43D3 host to 40 μg/ml valine (0.3 mM).

The degP41 (ΔPst1-kan$^R$) mutation was replaced using P1 transduction with a degP41 (ΔPst1-kan$^S$) mutation. A pro-AB::Tn10 which is linked to degP was introduced into 43D3. The proline auxotroph was transduced to prototrophy using P1 phage grown on a strain carrying the degP kan$^S$ mutation. Since degP is linked by cotransduction to fhuA, the new strain, 43E7, was confirmed to retain resistance to bacteriophage T1.

The wild-type alkaline phosphatase (APase) gene was re-introduced into this host background to capitalize on the benefits obtained from the phoS* mutation described below. P1 co-transduction of a Tn5 insertion in the proC gene with phoA$^+$ was used to reintroduce the wild-type alkaline phosphatase gene into this host background. P1 transduction to proline prototrophy restored the proC gene. The resulting strain, 44D6, regained alkaline phosphatase expression and maintained the Δ(argF-lac) mutation responsible for the Lac-phenotype.

A mutation which results in an altered phosphate binding protein, phoS* (T10Y) (U.S. Pat. No. 5,304,472) was introduced. The phoS* protein has a reduced affinity for phosphate in the medium. The result is that induction of the alkaline phosphatase promoter occurs at a higher phosphate concentration than the wild type. This allows product expression from the APase promoter without severely depriving the culture of phosphate. PhoS is linked by P1 cotransduction to ilv. A Tn10 insertion in the ilv gene was re-introduced by P1 transduction. The isoleucine/valine auxotrophy was transduced to prototrophy using P1 phage grown on a strain carrying the phoS* (T10Y) and ilvG2096$^R$ mutations. The presence of the phoS* mutation results in blue colonies on high-phosphate agar media containing the chromogenic substrate, 5-bromo-4-chloro-3-indolylphosphate. The resulting strain was 45F8.

The cyo::kan$^R$ (Oden et al., *Gene*, 96: 29–36 [1990]) mutation in the gene for cytochrome o oxidase was introduced by transduction. This mutation was constructed in vitro by replacing a portion of the cyo gene with a kanamycin-resistance gene. Introduction of this mutation prevents switching between the low- and high-affinity cytochrome oxidases, cyo and cyd, respectively (U.S. Pat. No. 5,342,763). The cytochrome-switching phenomenon can lead to dissolved oxygen instabilities and unsuccessful fermentation runs. The resulting strain was 45F9.

Finally, two mutations in carbohydrate utilization pathways were introduced to allow this host to be distinguished from other recombinant hosts by a simple carbohydrate utilization test. The rhaR (Moralejo et al., *J. Bacteriol.*, 175: 5585–5594 [1993]) mutation was introduced by P1 cotransduction with argE. An argE::Tn10 mutation was introduced.

The strain was restored to prototrophy using P1 phage grown on a strain carrying the rhaR mutation. The resulting strain, 46F1, was confirmed to be unable to utilize rhamnose as a carbon source.

The Δrbs7 (referenced above) mutation was introduced by P1 cotransduction with a linked Tn10 insertion in the ilv gene. The isoleucine/valine auxotrophy was transduced to prototrophy using P1 phage on a strain carrying the ilvG2096$^R$ mutation. The presence of the ribose utilization defect in the resulting strain, 46D5, was confirmed using minimal media containing ribose as a carbon source. Retention of the phoS* (T10Y) was also confirmed as described above.

A sample from the end of a 100-L fermentation was obtained using aseptic technique and was plated as described in Example I. CFU/ml for the production organism was $8.5 \times 10^{10}$. As indicated in Table 2, no colonies were detected on ribose-containing plates for $10^9$ cells plated or for any further dilutions plated. However, colonies were detected on minimal rhamnose-containing media at a level of $8.2 \times 10^2$ CFU/ml. Reversion of the rhamnose point mutation was observed at approximately one revertant in $10^8$ cells plated.

assay is approximately one contaminating organism in $10^6$ or $10^7$ cells plated.

TABLE 3

| | | Spiked Organisms | | | | |
|---|---|---|---|---|---|---|
| | Rhamnose minimal media Rha$^+$ Δrbs Δmal strain ($2.1 \times 10^9$ CFU/ml) | | | Ribose minimal media Rbs$^+$ Rha$^+$ strain ($1.02 \times 10^9$ CFU/ml) | | |
| Production organism CFU plated | Dilution | CFU Expected | CFU Observed | Dilution | CFU Expected | CFU Observed |
| $10^6$ | $10^{-6}$ | 210 | 146 | $10^{-6}$ | 102 | 94 |
| | $10^{-7}$ | 21 | 11 | $10^{-7}$ | 10 | 9 |
| | $10^{-8}$ | 2 | 1 | $10^{-8}$ | 1 | 1 |
| | $10^{-9}$ | 0 | 0 | $10^{-9}$ | 0 | 0 |
| $10^7$ | $10^{-6}$ | 210 | 141 | $10^{-6}$ | 102 | 121 |
| | $10^{-7}$ | 21 | 16 | $10^{-7}$ | 10 | 16 |
| | $10^{-8}$ | 2 | 1 | $10^{-8}$ | 1 | 3 |
| | $10^{-9}$ | 0 | 0 | $10^{-9}$ | 0 | 0 |

TABLE 2

Cross-host contamination testing for an IGF-I production organism

| Production Organism | Rhamnose Minimal Media | Ribose Minimal Media |
|---|---|---|
| 100 L (OD 164) | | |
| $8.5 \times 10^{10}$ CFU/ml | $8.2 \times 10^2$ CFU/ml | none |

The results of a spiking study are shown in Table 3. For the 46D5 host either $10^6$ or $10^7$ CFU were plated on rhamnose minimal media or ribose minimal media. Serial 10-fold dilutions of the spiked organism were made in PBS. The spiked organism was either a Rha$^+$ Δrbs Δmal (multiply marked strain) or a wild-type organism (Rha$^+$ Rbs$^+$ Mal$^+$). 0.1 ml of the $10^{-6}$, $10^{-7}$, $10^{-8}$ and $10^{-9}$ dilutions were plated along with the production organism. Plates were incubated at 37° C. for 48–72 hours. The expected results for detection of the spiked organisms were equivalent to the observed results for detection of the spiked organisms, within normal experimental error. In this example, where the production organism needs to be diluted to avoid detection of false positives (revertants or suppressors), the sensitivity of the Example III Multiply Marked Strain With Two Non-reverting Carbohydrate Mutations A highly sensitive test can be achieved if one uses a doubly marked strain with two non-reverting mutations. This strain is a derivative of the *E. coli* K-12 strain designated 48A4, with genotype W3110 ΔfhuA ΔmalE Δ(rbs7). The starting strain *E. coli* W3110 is a derivative of *E. coli* K-12 that is F$^-$ and lambda$^-$. It has been shown to carry an inversion of the chromosome between rrnD and rrnE. The fhuA gene (U.S. Pat. No. 5,304,472) was deleted from W3110 by imprecise excision of Tn10 following its insertion into the fhuA gene. The resulting strain, 1A2, is resistant to bacteriophage T1, T5, and 80. Two mutations in carbohydrate utilization pathways were introduced. A deletion of malE was constructed by PCR and incorporated into a plasmid vector, pS1080, containing beta-lactamase and levan sucrase. Bass et al., *J. Bacteriol.*, 178: 1154–1161 (1996). The plasmid was recombined by M13 transduction and carbenicillin resistance into the chromosome of a W3110 derivative that will not support independent replication of the plasmid vector (BW16824). Metcalf et al., *Gene,* 138: 1–7 (1994); Bass et al., supra. Strain 1A2 was then transduced to carbenicillin resistance with P1 phage grown on the strain carrying the malE deletion plasmid integrated into its chromosome. Sucrose-resistant derivatives were selected and screened for loss of carbenicillin resistance and inability to use maltose. The resulting strain, 46H9, was confirmed to carry the planned mal deletion using PCR.

The Δ(rbs7) mutation (referenced above) was introduced by P1 cotransduction with a linked Tn10 insertion in the ilv gene. A spontaneous Ilv$^+$ prototroph was obtained by plating on glucose minimal media. The resulting strain was designated 48A4.

A sample from an LB overnight culture was centrifuged and concentrated approximately 10-fold using aseptic technique. Serial 10-fold dilutions were made into PBS. 0.1 ml was plated onto minimal media (described above) containing 0.2%–0.4% of the carbon source indicated in Table 4. Plates were incubated at 37° C. for approximately 48 hours.

CFU/ml for the test organism, 48A4, were determined to be $2.2 \times 10^{10}$ CFU/ml. CFU from $10^9$ to $10^5$ per plate were plated. No colonies were observed as indicated in Table 4.

The results indicate the absence of reversion or suppression of the two carbohydrate markers. Thus, a culture containing $10^9$ CFU/plate of the desired organism could be plated and the sensitivity of the test for a doubly marked non-reverting organism such as 48A4 would be approximately one contaminating organism in $10^9$ cells plated.

TABLE 4

| 48A4 CFU plated | Colonies Detected | |
|---|---|---|
| | Ribose minimal media | Maltose minimal media |
| $2.2 \times 10^9$ | no colonies | no colonies |
| $2.2 \times 10^8$ | no colonies | no colonies |
| $2.2 \times 10^7$ | no colonies | no colonies |
| $2.2 \times 10^6$ | no colonies | no colonies |
| $2.2 \times 10^5$ | no colonies | no colonies |

Example IV

Detection of a Contaminating Auxotrophic Organism

A cross-host contaminating organism that has an amino acid or other auxotrophic requirement could also be detected by adjusting the media composition. In this example it is shown that a leucine auxotroph can be detected using the media described below. 26G5 is a derivative of *E. coli* K-12 W3110 ΔfhuA strain containing a deletion in leuA. This organism, which has a requirement for the amino acid leucine, was used for spiking studies shown below. Leucine was added to minimal media at a final concentration of 0.3 mM or was added as part of a mixture of components (complete supplements) which could support growth of most auxotrophic *E. coli* strains. The complete supplement is composed of components that are known not to be utilized by the *E. coli* organism as a sole carbon source. The components of the complete supplement include: 0.3 mM of the amino acids L-arginine, L-asparagine, L-aspartic acid, L-glycine, L-histidine, L-valine, L-leucine, L-methionine, L-threonine, L-isoleucine, L-glutamic, L-tryptophan, L-phenylalanine, and L-lysine; 15 μg/ml (0.1 mM) of hypoxanthine; vitamins (0.2 μg/ml of myo-inositol, 0.1 μg/ml of pantothenate, 0.1 μg/ml of niacinamide, 0.1 μg/ml of pyridoxal HCl, 0.1 μg/ml of choline chloride, 0.1 μg/ml of folic acid, 0.01 μg/ml of riboflavin, 0.34 μg/ml of para-aminobenzoic acid, and 0.5 μg/ml of thiamine); and trace elements (27 μg/ml of ferric chloride hexahydrate, 8 μg/ml of zinc sulfate, 7 μg/ml of cobalt chloride hexahydrate, 7 μg/ml of sodium molybdate, 8 μg/ml of cupric sulfate pentahydrate, 2 μg/ml of boric acid, and 5 μg/ml of manganese sulfate monohydrate).

The strain construction procedures for 46D5 and 48A4 are described in detail in Examples II and III, respectively. A sample from an LB overnight culture was centrifuged and concentrated approximately 10-fold using aseptic technique. Serial 10-fold dilutions were made in PBS. For the 46D5 host either $10^6$ or $10^7$ CFU were plated on rhamnose minimal media supplemented only with leucine or rhamnose minimal media with complete supplements.

For the 48A4 host $10^9$ CFU were plated on the maltose minimal media supplemented only with leucine or maltose minimal media with complete supplements. No colonies were detected for either organism in the absence of the spiked culture.

Serial 10-fold dilutions were made in PBS of the 26G5 leucine auxotrophic organism to represent a putative contaminant. A total of 0.1 ml of the $10^{-6}$, $10^{-7}$, $10^{-8}$, and $10^{-9}$ dilutions were plated along with the production organism. Plates were incubated at 37° C. for 48–72 hours. The results are shown in Table 5.

Spiking studies with a leucine auxotroph indicate that the test is as sensitive as one can expect from the number of spiked organisms plated onto a lawn of a non-utilizing organism. In the case where the production organism does not need to be diluted, the sensitivity is approximately one contaminating organism in $10^9$ cells plated. Where necessary, the production organism may need to be diluted to avoid detection of false positives (revertants or suppressors), and in this case the sensitivity is on the order of one contaminating organism in $10^6$ or $10^7$ cells plated. Individual supplementation of an amino acid such as leucine or a broader supplementation that would detect most auxotrophic *E. coli* strains gave similar results.

TABLE 5

| | Spiked Organism 26G5 ΔleuA ($2.2 \times 10^9$ CFU/ml) | | | | | |
|---|---|---|---|---|---|---|
| | Rha plus leucine | | | Rha plus supplements | | |
| Production Organism CFU plated | Dilution of Spiked Organism | CFU Expected | CFU Observed | Dilution of Spiked Organism | CFU Expected | CFU Observed |
| 46D5 Δrbs ΔrhaR | | | | | | |
| plated $10^6$ | $10^{-6}$ | 220 | 190 | $10^{-6}$ | 220 | 144 |
| | $10^{-7}$ | 22 | 15 | $10^{-7}$ | 22 | 25 |
| | $10^{-8}$ | 2 | 3 | $10^{-8}$ | 2 | 2 |
| | $10^{-9}$ | 0 | 0 | $10^{-9}$ | 0 | 0 |
| plated $10^7$ | $10^{-6}$ | 220 | 186 | $10^{-6}$ | 220 | 198 |
| | $10^{-7}$ | 22 | 21 | $10^{-7}$ | 22 | 14 |
| | $10^{-8}$ | 2 | 3 | $10^{-8}$ | 2 | 2 |
| | $10^{-9}$ | 0 | 0 | $10^{-9}$ | 0 | 0 |

TABLE 5-continued

| | Maltose plus leucine | | | Maltose plus supplements | | |
|---|---|---|---|---|---|---|
| Production Organism CFU plated | Dilution of Spiked Organism | CFU Expected | CFU Observed | Dilution of Spiked Organism | CFU Expected | CFU Observed |
| 48A4 $\Delta$mal $\Delta$rbs | | | | | | |
| plated $10^9$ | $10^{-6}$ | 220 | 131 | $10^{-6}$ | 220 | 246 |
| | $10^{-7}$ | 22 | 13 | $10^{-7}$ | 22 | 21 |
| | $10^{-8}$ | 2 | 0 | $10^{-8}$ | 2 | 1 |
| | $10^{-9}$ | 0 | 0 | $10^{-9}$ | 0 | 0 |

What is claimed is:

1. A process for enumerating individual colonies in a mixture of cultured microbial host cell strains contained in a single culturing vessel which strains utilize more than one carbohydrate source as a substrate and have been genetically engineered by altering the strains' genotypes so that they do not utilize a set of n−1 carbohydrate sources as substrates, where n is the number of said microbial host cell strains, which set of carbohydrate sources is different for each genetic marking employed, which process comprises:

(a) culturing in the vessel the host cell strains;
   (b) diluting an isolated sample of culture until a countable number of viable cells will be present when the sample is plated;
   (c) plating the diluted sample of culture onto culture media supplemented with a carbohydrate source only utilized by one of the host cell strains as a substrate;
   (d) incubating the plated cells at a temperature and for a time sufficient for any positive colony to grow to a detectable level; and
   (e) counting the number of colonies growing on the supplemented culture media;

wherein steps (c) through (e) are carried out for each colony of strain to be enumerated, and wherein the carbohydrate source supplementing the media is different for each strain.

2. The process of claim 1 wherein the microbial host cell strains are bacterial strains.

* * * * *